(12) United States Patent
Labib et al.

(10) Patent No.: US 6,619,302 B2
(45) Date of Patent: Sep. 16, 2003

(54) CLEANING COMPOSITION AND APPARATUS FOR REMOVING BIOFILM AND DEBRIS FROM LINES AND TUBING AND METHOD THEREFOR

(75) Inventors: Mohamed Emam Labib, Princeton, NJ (US); Ching-Yue Lai, Lawrenceville, NJ (US)

(73) Assignee: Princeton Trade & Technology, INC, Princeton, NJ (US)

( * ) Notice: Subject to any disclaimer, the term of this patent is extended or adjusted under 35 U.S.C. 154(b) by 0 days.

(21) Appl. No.: 09/162,698

(22) Filed: Sep. 29, 1998

(65) Prior Publication Data

US 2001/0047813 A1 Dec. 6, 2001

Related U.S. Application Data

(62) Division of application No. 08/880,662, filed on Jun. 23, 1997, now Pat. No. 6,027,572.

(51) Int. Cl.[7] .............................................. B08B 3/02
(52) U.S. Cl. ............................ 134/102.2; 134/166 C; 134/169 C
(58) Field of Search ................... 134/102.2, 102.3, 134/166 C, 169 C, 168 C; 136/22.1, 22.11, 22.12, 22.18, 102.1, 100.1

(56) References Cited

U.S. PATENT DOCUMENTS

| | | | | |
|---|---|---|---|---|
| 2,809,429 A | * | 10/1957 | Cerveris | |
| 2,875,521 A | * | 3/1959 | Tascher | |
| 3,182,670 A | * | 5/1965 | Howell | |
| 3,625,231 A | | 12/1971 | Littrell, Jr. | .................. 134/102 |
| 4,169,123 A | | 9/1979 | Moore et al. | ................. 422/28 |
| 4,219,333 A | | 8/1980 | Harris | ........................... 8/137 |
| 4,222,346 A | * | 9/1980 | Reisgies | |
| 4,311,618 A | | 1/1982 | Schafer-Burkhard | ........ 252/542 |
| 4,477,438 A | | 10/1984 | Willcockson et al. | ........ 424/130 |
| 4,525,220 A | | 6/1985 | Sasa et al. | ................. 134/22.18 |
| 4,710,233 A | | 12/1987 | Hohmann et al. | ............. 134/1 |
| 4,744,951 A | | 5/1988 | Cummings et al. | ........... 422/28 |
| 4,752,444 A | * | 6/1988 | Bowen et al. | |
| 4,776,794 A | * | 10/1988 | Meller | |

(List continued on next page.)

FOREIGN PATENT DOCUMENTS

| | | | |
|---|---|---|---|
| DE | 893595 | 10/1953 | |
| EP | 490117 A1 | 12/1990 | ............. B08B/9/06 |
| EP | 634229 B1 | 7/1993 | ............. B08B/9/06 |
| JP | 63-12933 | * 1/1988 | |
| SU | 1042826 A | 2/1981 | ............. B08B/9/02 |

OTHER PUBLICATIONS

WO 96/29098 Sep.–1996.*
S. W. Yuan, "Foundations of Fluid Mechanics", Prentice–Hall Inc,1967, pp357–363.

(List continued on next page.)

Primary Examiner—Frankie L. Stinson
(74) Attorney, Agent, or Firm—Birgit E. Morris (57) ABSTRACT

Biofilm and debris can be removed from the interior and exterior surfaces of small bore tubing by passing an aqueous cleaning solution of water, one or more surfactants and preferably a source of hydrogen peroxide, optionally including small inert solid particles, together with a gas under pressure, to create a turbulent flow within the tubing that loosens the biofilm and debris so that they can be flushed from the tubing. When the exterior surfaces of tubing are to be cleaned, the tubing is inserted in a sleeve fitted with an adaptor that provides a pressure-tight seal between the tubing and the sleeve.

18 Claims, 10 Drawing Sheets

U.S. PATENT DOCUMENTS

| | | | |
|---|---|---|---|
| 4,863,688 A | | 9/1989 | Schmidt et al. ................ 422/28 |
| 4,874,002 A | * | 10/1989 | Sundholm ............... 134/169 C |
| 4,892,112 A | * | 1/1990 | Knetsch |
| 4,988,485 A | * | 1/1991 | Bene |
| 5,007,461 A | | 4/1991 | Naf .......................... 134/22.12 |
| 5,045,352 A | | 9/1991 | Mueller ................... 134/22.12 |
| 5,077,008 A | | 12/1991 | Kralovic et al. ............... 422/37 |
| 5,107,875 A | * | 4/1992 | Sundholm ............... 134/166 C |
| 5,137,689 A | * | 8/1992 | Cantrell |
| 5,159,956 A | * | 11/1992 | Kurihara ................. 134/169 C |
| 5,197,499 A | | 3/1993 | Bodenmiller et al. |
| 5,244,468 A | | 9/1993 | Harris ........................... 8/137 |
| 5,287,867 A | * | 2/1994 | Plummer et al. ........ 134/102.1 |
| 5,395,456 A | | 3/1995 | Abrams et al. .......... 134/22.14 |
| 5,403,479 A | | 4/1995 | Smith et al. |
| 5,408,991 A | * | 4/1995 | Iida et al. ....................... 128/4 |
| 5,419,347 A | * | 5/1995 | Carruth |
| 5,423,917 A | * | 6/1995 | Garica, Jr. ............... 134/22.11 |
| 5,425,815 A | | 6/1995 | Parker et al. ................. 134/26 |
| 5,462,605 A | * | 10/1995 | Szucs ...................... 134/102.1 |
| 5,494,530 A | | 2/1996 | Graf ........................ 134/22.12 |
| 5,505,218 A | * | 4/1996 | Steinhauser |
| 5,595,344 A | * | 1/1997 | Starnes |
| 5,615,695 A | * | 4/1997 | Chambers ............... 134/169 C |
| 5,674,323 A | * | 10/1997 | Garcia |
| 5,699,817 A | * | 12/1997 | Bankert et al. .......... 134/102.2 |
| 5,723,090 A | * | 3/1998 | Beerstecher et al. |
| 5,795,404 A | | 8/1998 | Murphy et al. .......... 134/22.18 |
| 5,837,204 A | * | 11/1998 | Prevost ................... 134/169 C |
| 5,858,114 A | * | 1/1999 | Board et al. ............. 134/169 C |
| 5,925,257 A | * | 7/1999 | Albelda et al. |
| 6,019,117 A | * | 2/2000 | Detsch et al. |
| 6,142,170 A | * | 11/2000 | Belfer et al. |
| 6,423,152 B1 | | 7/2002 | Landaas ...................... 134/10 |

OTHER PUBLICATIONS

Plummer Design and Technologies, Illinois Waste Management and Research Center,1991, Abstract.

Barajas et al, "The Effects of Contact Angle on Two–Phase Flow in Capillary Tubes", Int. J Multiphase Flow, vol. 19 pp337–346, 1993.

Hobbe et al, "Use of Nuclepore Filters for counting Bacteria by Fluorescence Microscopy", Applied and Environmental Microbiology, vol. 33, No. 5, May, 19787, pp 1226–1228.

Kogure et al "A tentative direct microscopic method forcounting living marine bacteria", Can. J. Microbiol. vol. 25, 1975, pp 415–420.

* cited by examiner

CLEANING COMPOSITION AND APPARATUS FOR REMOVING BIOFILM AND DEBRIS FROM LINES AND TUBING AND METHOD THEREFOR

This application is a Divisional application of Ser. No. 08/880,662, filed Jun. 23, 1997, now U.S. Pat. No. 6,027,572.

This invention relates to a mixed-phase cleaning solution and method for removing bacteria with pathogenic potential and other microorganisms, debris, tissue, food particles and the like from lines and tubing, and to an apparatus that delivers the mixed-phase cleaning solution under pressure to the lines and tubing to be cleaned.

BACKGROUND OF THE INVENTION

Small bore tubing that delivers ordinary running water, purified or not, to fixtures such as dental units, develop bacterial and fungal growth from the water on their interior surfaces, as is well known. Bacteria present in the water strongly adhere to tubing surfaces and then grow laterally, forming what is known as biofilm. Biofilm is apparent to the touch as a slimy film which has been analyzed and found to be bacterial growth.

Several prior art workers have identified various bacteria included in these biofilms, which include several bacteria having pathogenic potential, such as Flavobacterium, Moraxella, Achromobacter, Pseudomonas, Alcaligenes, Micrococcus and Legionella. All of these bacteria have the potential to cause infections in humans, and legionella, which is highly resistant to antibiotics, is of particular concern since infection can be fatal. Organisms such as legionella can also be inhaled from contaminated water spray during dental or other medical treatment.

Dental unit tubing that carries rinse water to the mouth of patients has been determined to contain over one million ($1 \times 10^6$) colony forming units of bacteria per milliliter of water (CFU/ml) after one week of use. Thus these water lines and tubing must be periodically cleaned to ensure the removal of this biofilm on the walls of the tubing to prevent infection. The potential for infection of immuno compromised patients is also a major concern. If the patient has any open wounds in the mouth, the danger of infection is of course much higher.

Biofilms are very difficult to remove from tubing however. The biofilm is strongly adherent to smooth tubing surfaces, whether the tubing is made from natural or synthetic materials such as rubber-based materials, polyethylene, polytetrafluoroethylene and the like. Treatment with disinfectant and biocidal agents may kill the bacteria and so remove the biofilm. However, these agents do not readily diffuse into the biofilm which strongly adheres to the tubing walls, and thus removal is generally only partial and the biofilm returns quite rapidly. Reduction of the level of bacteria present in water delivery systems to below 200 CFU/ml has been suggested by the American Dental Association.

Other applications employing small bore tubing that must be periodically cleaned include internal endoscopy tubing, catheter tubing, sterile filling ports, and tubing used for sterile manufacturing, food processing and the like. These types of tubing may contain, in addition to biofilm, food particles, tissue particles, mucous, blood and the like, which is referred to hereinafter as "debris". Such tubing also must be thoroughly cleaned, these between each and every use, to prevent infection from one patient to another.

Guidelines for cleaning gastrointestinal endoscopy units promulgated by the American Society for Gastrointestinal Endoscopy include a multi-step method for cleaning tubing between patients to prevent infection. First, mechanical cleaning with a brush is performed, using a detergent solution, soon after use. The tubing is then rinsed with water and then a sterilization is carried out using a disinfecting solution such as a gluteraldehyde solution. The tubing is then rinsed with water again and then dried with forced air.

Other applications for the present invention are respirators, both neonatal and adult, which must be cleaned about every 8 hours or so. Such cleaning is expensive, but necessary.

Thus an improved cleaning composition and method for removing biofilm and debris from interior and external tubing surfaces in a cost effective manner and for preventing or delaying biofilm reoccurrence, and an apparatus to deliver these cleaning solutions to the lines and tubing that have become contaminated, would be highly desirable.

SUMMARY OF THE INVENTION

In accordance with the present invention, a combination of pressurized gas and a suitable aqueous cleaning solution is used to create a turbulent environment on or in a tubing having a biofilm or debris on interior or exterior surfaces, that completely removes the biofilm and debris. A suitable aqueous cleaning solution comprises water and a surfactant. An oxidizing agent and a biocidal agent can also be added. Inert particles that can provide a scrubbing action can also be added advantageously to the aqueous cleaning solution. This aqueous cleaning composition is delivered to the tubing to be cleaned by means of compressed gas, thus making a mixed-phase system, that provides a turbulent flow along the walls of the tubing that aids in loosening the biofilm and debris from the surfaces of the tubing, and aids in flushing the loosened materials from the tubing.

The invention also includes an apparatus for delivering the above mixed-phase cleaning solution to the interior of small bore tubing and lines and combining it with a gas under pressure. The compressed gas-aqueous cleaning solution combination develops turbulent flow inside the tubing that aids in loosening the biofilm from the interior surfaces of tubing so that it can be readily removed by flushing and rinsing with water.

The invention also includes an apparatus for delivering the above cleaning solution to the exterior surfaces of small bore tubing and lines, by encapsulating the tubing in a pressure-resistant sleeve having an adaptor that provides a pressure-tight seal between the cleaning solution-pressurized gas mixture and the tubing. The apparatus includes a mixing chamber for mixing the aqueous solution, optional solid particles and a gas under pressure for delivery to the lines and tubing to be cleaned.

DETAILED DESCRIPTION OF THE INVENTION

The aqueous cleaning solution useful herein contains water and a surfactant that, when mixed under pressure with a gas such as air, acts to loosen organic residues from tubing surfaces so they can be rinsed away. Since the cleaning solution is water-based, environmental problems relating to waste disposal are reduced or non-existent.

The aqueous cleaning solution can comprise water and a surfactant alone, but preferably includes an oxidizing agent, such as a hydrogen peroxide source.

Suitable surfactants can be nonionic, anionic or cationic, or mixtures thereof. Any surfactant that is compatible with water or aqueous solutions can be used, generally in a concentration of up to about 5% by weight of the cleaning solution.

Suitable anionic surfactants include for example alkyl sulfates and sulfonates such as sodium dodecyl sulfate. Nonionic surfactants can be added to increase the wetting of the organic material to be removed, and to improve the quality of the foam generated when the aqueous surfactant-containing solution is mixed with a gas under pressure.

Cationic surfactants, such as quaternary amines, have a strong interaction with glycoproteins and bacterial cell walls present in biofilms, and thus solubilize the bacterial and fungal matter in the biofilm. Cationic surfactants are also known that have disinfectant properties.

These surfactants provide a foaming action to the aqueous solution which helps to provide a turbulent flow in the tubing to be cleaned, and also aids in loosening the biofilm or debris from the tubing surface. In particular, quaternary amine surfactants produce small bubbles in solution that further aid in forming a turbulent flow in the gas-cleaning solution mixture during cleaning, adding a scrubbing action against the biofilm that aids in its effective and efficient removal.

The presence of an oxidizing agent is also believed to aid in loosening the biofilm from the interior and exterior walls of tubing and lines. Suitable oxidizing agents include aqueous hydrogen peroxide solutions, or peroxy compounds such as perborates, periodates and peroxycarboxylic acids that produce hydrogen peroxide in situ in an aqueous solution. Solid oxidizing agents, such as peroxycarbonates and the like, may also provide a further scrubbing action.

Further, oxidizing agents have biocidal properties that not only aid in efficiently reducing bacterial material from tubing walls, but also reduce the re-occurrence of biofilm. Mixing a peroxide-surfactant solution with compressed air produces a thick froth, enhanced by the peroxide, in the tubing which removes biofilm more effectively than water and air alone. The oxidizing agents are suitably present in amounts of up to about 15% by weight of the aqueous solution, preferably about 3–15% by weight.

Inert particles can also be added advantageously to the aqueous cleaning solution of the invention to provide a further scrubbing action to the tubing walls. Hard insoluble particles, such as of silica, alumina and titania, will provide the most effective scrubbing action together with surfactant foams. Soft insoluble inert particles such as calcium carbonate, preferably having a small particle size such as 10–300 microns, can advantageously be used. These materials are normally used already as abrasives for cleaning teeth or removing plaque and for polishing teeth and gums. Water soluble particles, such as sodium bicarbonate, can also be added. Since removal of biofilm takes place rapidly in accordance with the invention, some scrubbing action by the water soluble particles is obtained prior to their dissolution. The fact that the particles are water soluble means that they dissolve during the rinsing or flushing step, so that the particles are removed from the tubing surfaces in solution, thus reducing the number of solid particles that must be flushed out of the tubing after cleaning.

A sufficient amount of inert, insoluble particles can be added to the above cleaning solution to provide increased erosion of the biofilm by impact of the particles on the walls of the tubing to be cleaned in a turbulent environment. However, in order to remove biofilm, the particle size of the inert particles should be on the order of 10–300 microns, which may be somewhat larger than particles used in tooth pastes for example. The particle shape is not critical, but may be adjusted to maximize the effectiveness of the present process. For example, an irregularly shaped particle may be preferred to a smooth walled particle to increase the scrubbing action of the mixture. The particles preferably are hydrophobic so that they can be carried along in the cleaning solution by air bubbles. For example, generally up to about 20% by weight of inert particles are suitably added to the cleaning solution.

The temperature of use of the cleaning mixture of the invention can vary from about 0–50° C.

The cleaning solution and the inert particles used herein are safe and non-toxic. Most of the ingredients are already used in present-day dental practices and thus present no danger to patients. The cleaning solution can be discharged into municipal sewage systems. The cleaning solution is also safe, i.e., non-toxic and non-carcinogenic, and is non-corrosive to commonly available plastics such as polyvinychloride, polyolefin and polytetrafluoroethylene tubing.

The cleaning solution is used together with a pressurized gas that provides turbulence of the cleaning solution inside the tubing. Although the invention is hereinafter described using air as the gas, other gases can be substituted such as oxygen, nitrogen, carbon dioxide, noble gases such as argon and the like. Such gases may be stored under pressure in cylinders, or available from in-house gas sources.

The mixture charged to the tubing to be cleaned preferably includes a surfactant that produces bubbles or froth in the aqueous solution, a surfactant that produces a foaming action to the aqueous solution, and air under pressure. This mixed-phase mixture is charged to the small bore tubing to be cleaned in a sufficient volume to loosen and remove biofilm in a short time, i.e., about 3–10 minutes. The volume of the mixed-phase cleaning solution can thus be maximized for various applications.

To further increase the scrubbing action of the above mixture, the pressurized air can be pulsed.

The air or other pressurized gas is delivered under a pressure of above about 25 psi, preferably at a pressure of about 30 to 60 psi for dental tubing. However, the pressure range is not critical and can be adjusted to be higher according to the tubing diameter.

After the small bore tubing has loosened the biofilm and/or debris, water alone, together with pressurized air, can be used to remove all solid materials from the tubing. This flushing step generally takes another 3 or more minutes.

The invention will be first described in the Examples in terms of cleaning dental tubing that supplies cleaning water under pressure. The pressure is supplied by an air compressor that can continuously supply up to 80–100 psi of compressed air. This pressure is stepped down to about 30–60 psi prior to entry of the cleaning composition to the hand cleaning syringe used by the dental practitioner. As a comparison, water is generally delivered by municipal water systems at a pressure of about 25 psi.

Figure 1:
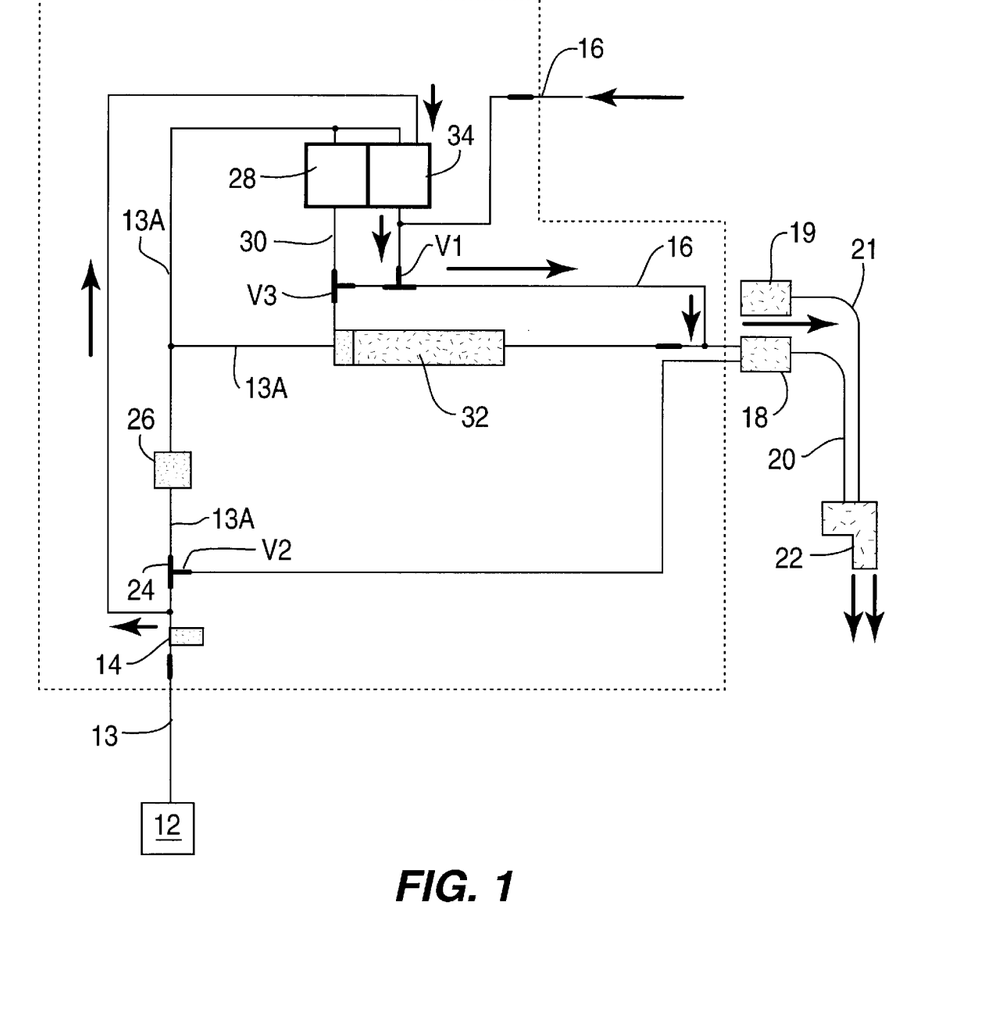
FIG. 1 is a schematic view of an aqueous cleaning composition delivery system of the present invention.

FIG. 1 is a schematic diagram of a modified coolant and irrigation apparatus for use by a dental practitioner. The conventional system includes an air compressor 12, an air line 13, a pressure regulator 14, a water line 16 for adding water or other aqueous solution to the compressed air in line 13, an air adaptor 18 and a water adaptor 19 to permit the dental practitioner to adjust the volumes of air in line 20 and water in line 21 delivered to a hand held fixture 22.

In accordance with the present invention, the conventional apparatus is modified to deliver the present cleaning solution to water line 21 to clean it.

A three way valve 24 is used to direct the pressurized air to air line 13A. A solenoid valve 26 is inserted into line 13A to impart a pulsing action to the pressurized air.

A pressurized container 28 that is refillable stores the cleaning solution of the invention. An air tight cap (not shown) permits the cleaning solution to be replaced and line 13A permits pressurized air to enter the container 28. The outlet line 30 is connected to a mixing chamber 32.

The mixing chamber 32 is connected to the pressurized air line 13A and to the cleaning solution outlet line 30. The cleaning solution and pressurized air are mixed in the mixing chamber 32 to create a turbulent mixture or froth depending on the ratio of air to cleaning solution, which can be adjusted.

Additional pressurized containers can be included. As shown in FIG. 1, a container 34 is connected to water line 16 and can include a biocide for example. The outlet from the container 34 can be directly connected to water line 16 or can be connected to the mixing chamber 32 for addition to the cleaning solution mixture.

A water source can be connected to the water line 16 or to the mixing chamber 32 to flush the dental water line 21 with water subsequent to cleaning with the cleaning solution of the invention.

A conventional control panel (not shown) can be used to regulate the air pressure in the system, to turn the solenoid valve 26 to impart a pulsating action to the compressed air, to control the temperature of the solutions, to control the three-way valves during regular dental unit operation, during cleaning and during flushing operations, to add biocide solution from the chamber 34 and the like. An alert light can be included to alert attendants that it is time to clean the dental tubing. The above system can be enclosed in a suitable housing if desired.

Thus during the cleaning cycle, the top water line 36 is shut off via valve V1 and compressed air is directed to the container 28 via valve V2. The solenoid valve 26 is activated to create a pulsating action to the compressed air which is passed to the container 28, and to the additional container 34 if required. A froth is formed in the mixing chamber 32 and is forced into the dental unit adaptor 19 to the dental tubing water line 21.

During the rinsing or flushing cycle, cleaning solution is shut off in line 30 via valve V3 and biocide or an alkaline peroxide solution and water can be directed to the mixing chamber 32 together with pulsating compressed air through line 13A. The pressurized water is passed through the dental tubing 21 to flush out cleaning solution, loosened biofilm and any solid particles or debris remaining in the tubing 21. The addition of a biocide and/or a peroxide may increase the time period that elapses before biofilm starts to re-form.

At the end of the flushing cycle, normal operation of the dental unit is resumed, using tap water alone or tap water including a biocide stored in container 34.

The cleaning, flushing and normal operation cycles are each continued for a certain period of time, as predetermined by the manufacturer or the practitioner.

The turbulent flow in the mixing chamber 32 provides bubbles or froth patterns by manipulating the ratio of air:liquid:particles and the flow speeds of the cleaning solution and compressed air. The compressed air creates liquid droplets, or suspends any solid particles in the cleaning solution, and thus produces an effective method of eroding the biofilm via a dynamic impact of the solution and froth or inert particles on the tubing walls.

As an example, air forced through a 1.8 mm diameter tubing, using 30–60 psi air pressure, has a Reynolds number between about 9700 and 15,000, which is considered to be turbulent in a pipe-type geometry. The addition of inert particles or liquid droplets to the cleaning solution further increases the cleaning effectiveness of the solution. When the biofilm has a thickness of 5–10 microns, the relationship between the applied air pressure and the friction force can be estimated in accordance with known one dimensional energy equations.

Calculated and measured velocities in an 8 foot long dental tubing 1.8 mm in diameter were in good agreement with each other.

Further, the fact that some dental tubing is continuously curled is an excellent geometry for the present cleaning method because it causes random impact of the air, solid particles and solution against the tubing walls to loosen and erode the biofilm rapidly and completely.

The invention will be further described in the following Examples 1–6 with respect to cleaning dental tubing, but the invention is not meant to be limited to the details described therein. In the Examples, percent is by weight unless otherwise noted.

EXAMPLE 1

Figure 2:
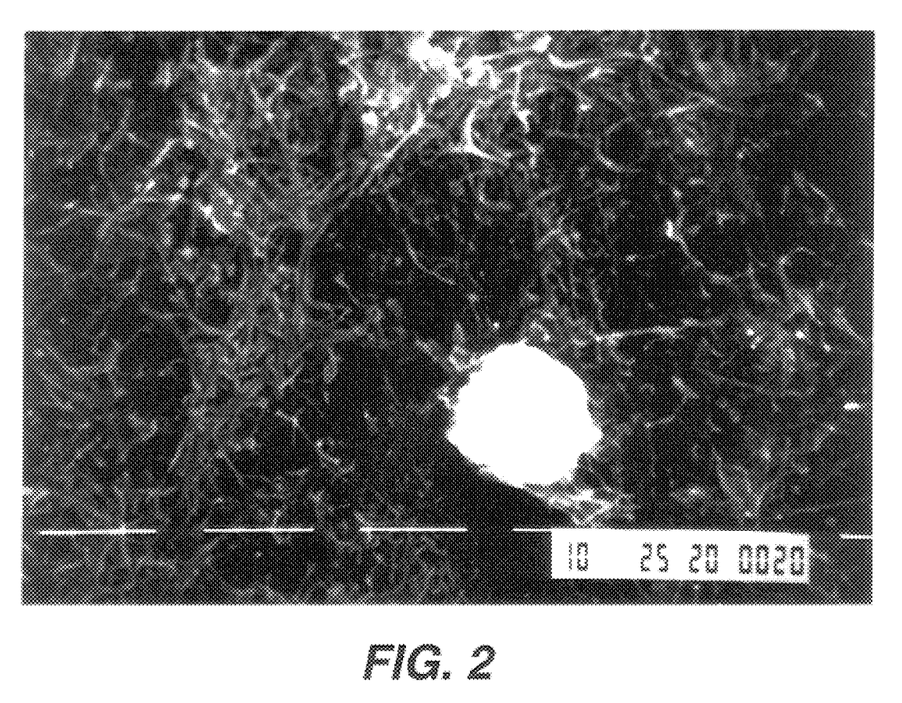
FIG. 2 is a high magnification photomicrograph of the inside wall of tubing having a biofilm thereon used in a dental unit, which biofilm is about one year old.

A portion of dental tubing having a biofilm about one year old on its interior surface is shown in FIG. 2. The biofilm completely covers the interior surface of the tubing and consists of about 200,000 colonies/cm of bacteria.

A three foot section of the tubing was treated in accordance with the invention using a cleaning solution of 3% aqueous hydrogen peroxide containing 5% by weight of inert particles of calcium carbonate 50–100 microns in size, and surfactants including about 2% of an anionic surfactant, sodium dodecyl sulfate, and about 1% of a nonionic surfactant. The cleaning solution was added to the mixing chamber 28 of FIG. 1 and air was added to the mixing chamber from a 1 HP air compressor regulated at 30–60 psi, the air being continuously pulsed. The amount of air and the pulse rate were regulated to optimize mixing of the ingredients and the turbulence generated inside the tubing. The mixture was passed to the dental tubing to permit turbulent cleaning of the tubing.

Figure 3:
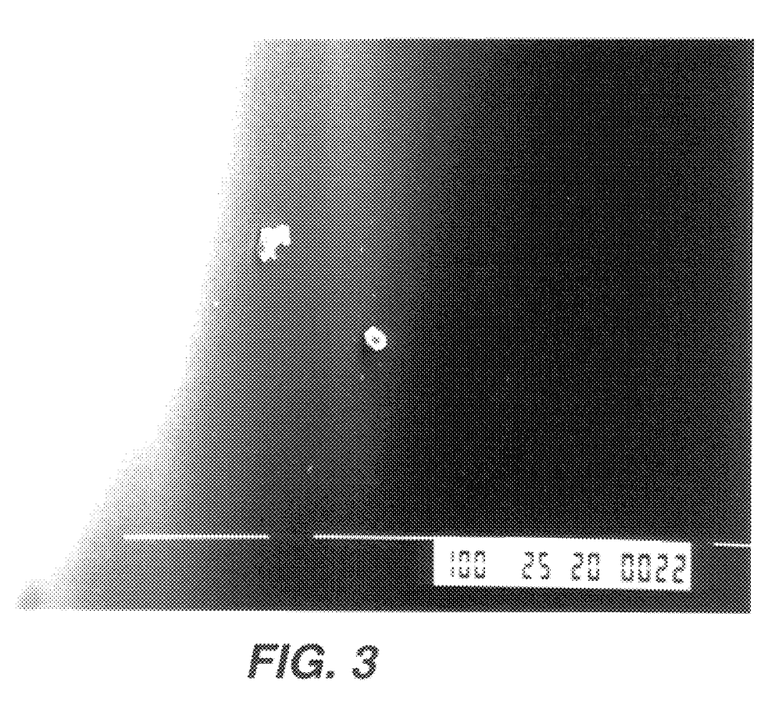
FIG. 3 is a photograph of an overall view of the interior wall of dental tubing after cleaning in accordance with the invention.

The tubing was then flushed with distilled water. The interior surface of the cleaned tubing is shown in FIG. 3. It is apparent that the biofilm has been completely removed.

The cleaned tubing was tested for bacteria by scraping the interior surface of a section of the tubing 2.5 cm long and collecting water in that portion of the tube as follows. The tubing was cut in half, about 1.25 cm in length, and three pieces were stored at 4° C. The lumen of each piece was scraped 15 times with the tip of a sterile scalpel blade to remove any bacteria and the scalpel and the tubing were agitated in water for one minute to suspend any bacteria present. The resultant suspension was diluted 10 fold and spread onto dilute peptone agar plates using distilled water. The water in the tubing was also diluted and plated. The plates were incubated for two weeks at 25° C. and the bacteria colonies counted and identified according to conventional practice, including Gram strain calitose reaction, oxidase and glucose fermentation tests. The total number of bacteria and the total number of viable bacteria were counted according to the procedure of Hobbe et al, Applied & Environmental Microbiology, May, 1977 pp 1225–1228; and Kogure et al, Can. J. of Microbiology Vol. 25, pp 415–420 (1979).

The cleaned tubing had only 280 colonies/cm of tubing, whereas untreated tubing had about 200,000 colonies/cm of tubing. Thus a reduction in bacterial count of one thousand times was obtained. The large white particles in FIG. 4 are believed to be deposits due to water hardness that accumulate over a long period of time.

EXAMPLE 2

A cleaning solution was made by mixing 50 grams of calcium carbonate particles having a particle size of 10–100 microns into 450 ml of a solution containing 3% by weight of hydrogen peroxide solution, 2% by weight of a surfactant, sodium dodecyl sulfate and 1% of a nonionic surfactant.

Figure 4:
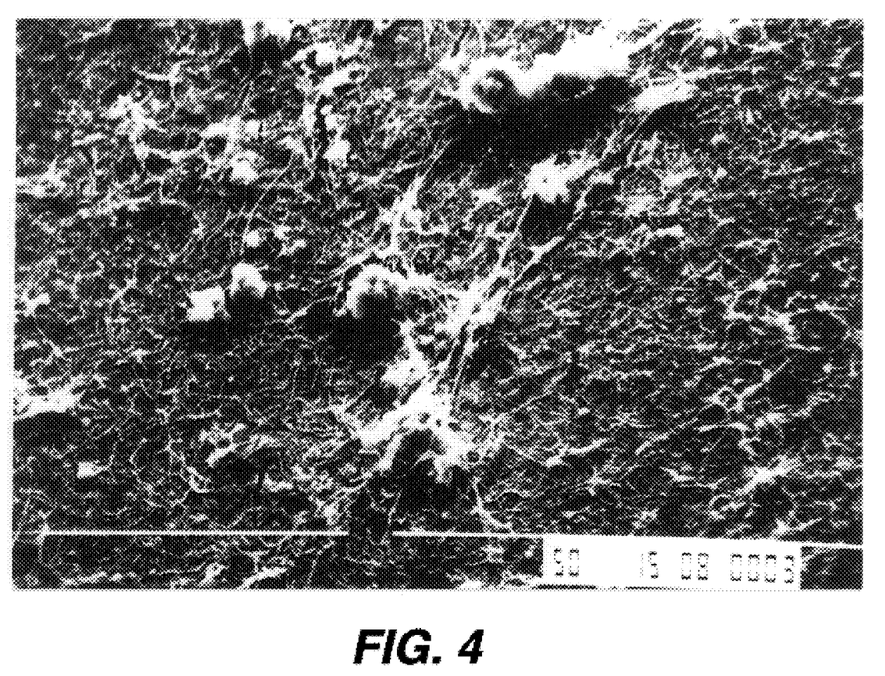
FIG. 4 is a photograph of the interior wall of another dental tubing prior to treatment according to the invention.

The above mixture was introduced into a used dental tubing 3 feet long and 1.8 mm in diameter having a biofilm thereon, as shown in FIG. 4, together with air supplied by a compressor set between 30 and 60 psi. The cleaning composition was flushed through the tubing for about 3 minutes.

The tubing was then flushed with 200 ml of distilled water.

The number of bacterial colonies in the tubing decreased from an initial value of $7.15 \times 10^5$ per linear cm of tubing down to zero after cleaning. The CFU/ml of water flowing in the tube was reduced from an initial value of $3.19 \times 10^6$ to zero after cleaning.

Figure 5:
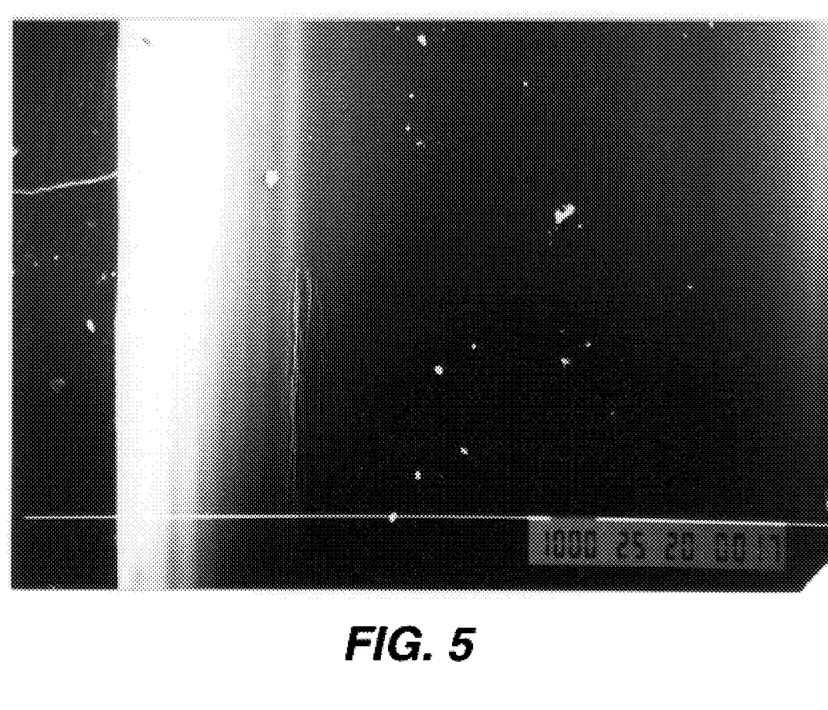
FIG. 5 is a photograph of an overall view of the interior wall of the dental tubing of FIG. 4 after treatment according to the invention.

The SEM photograph of FIG. 5 is an overall view of the interior wall of the tubing after treatment. FIG. 5 shows a complete removal of biofilm in the lumen of the tubing. The bare surface of the tubing was free of any debris or biofilm.

EXAMPLE 3

576 Milliliters of 3% by weight of aqueous hydrogen peroxide solution was admixed with 2% by weight of sodium dodecyl sulfate surfactant. The cleaning reagent was introduced into used dental tubing with air supplied by a compressor set at a pressure of 30 to 60 psi. After treatment for three minutes, the tubing was flushed with 200 ml of water.

The number of bacterial colonies per cm of tubing after culture decreased from an initial value of $1 \times 10^5$ to zero. The CFU/ml of the water decreased from an initial value of $3.01 \times 10^6$ to zero.

Figure 6:
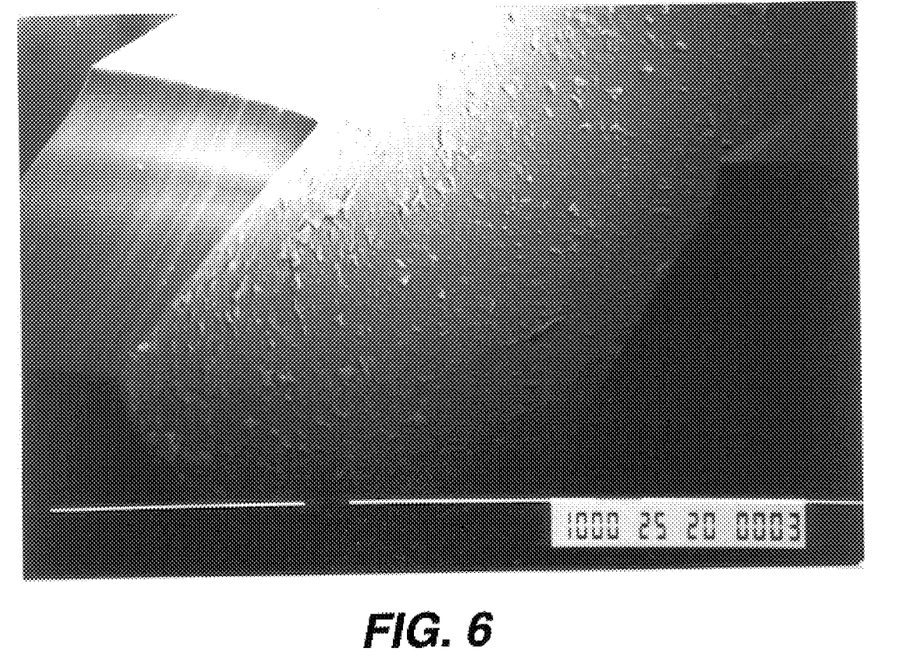
FIG. 6 is a photograph of an overall view of the interior wall of another dental tubing prior to treatment according to the invention.
Figure 7:
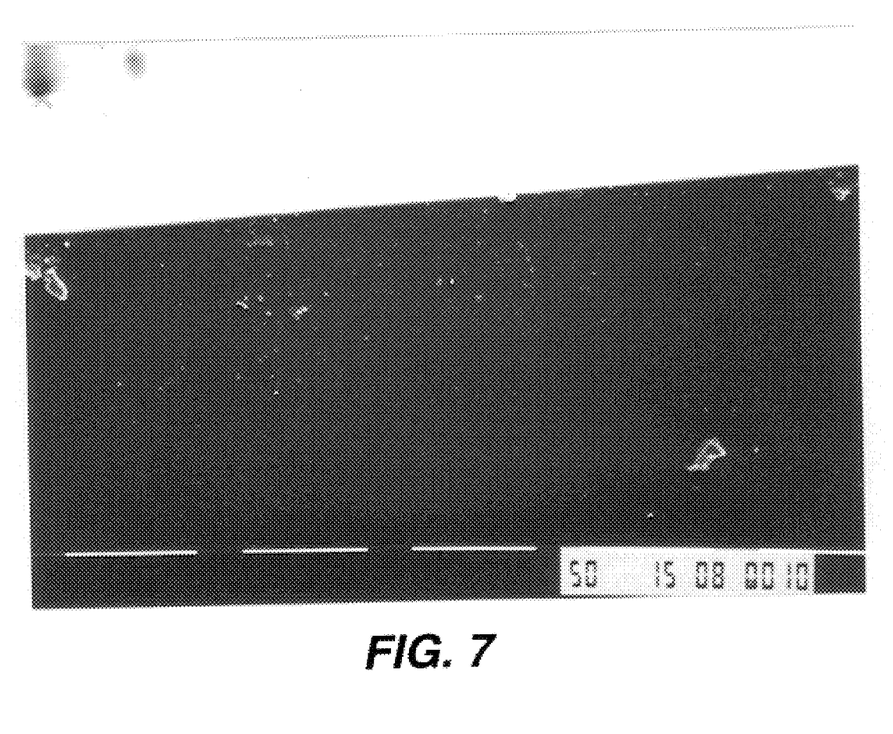
FIG. 7 is a photograph of the interior wall of a portion of the dental tubing of FIG. 6 after treatment.

FIG. 6 is a photograph of the interior wall of the tubing prior to treatment. FIG. 7 is a photograph of the interior wall of the tubing after treatment.

Thus in the presence of hydrogen peroxide, surfactant and air under a preselected pressure, complete cleaning was achieved even in the absence of solid particles.

EXAMPLE 4

The procedure of Example 2 was followed except substituting distilled water for the hydrogen peroxide solution.

The CFU/cm decreased from an initial value of $4 \times 10^5$ to zero. Thus a mixture of water, surfactant, abrasive particles and air under a preselected pressure was sufficient to remove the biofilm from the tubing.

Figure 8:
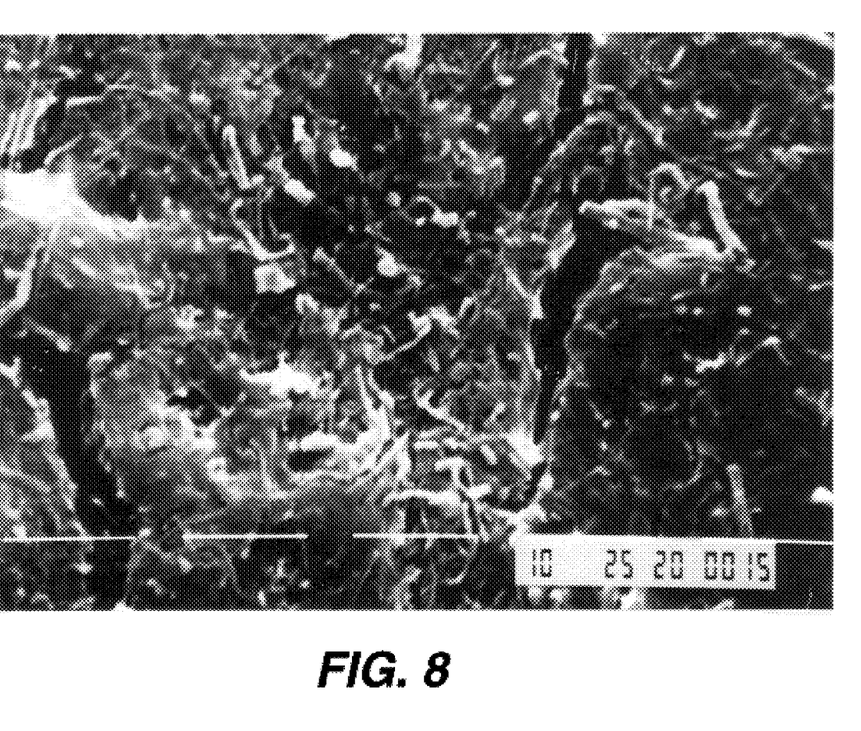
FIG. 8 is a photograph of still another dental tubing prior to treatment according to the invention.

FIG. 8 is a photograph of the interior surface of the tubing prior to treatment.

Figure 9:
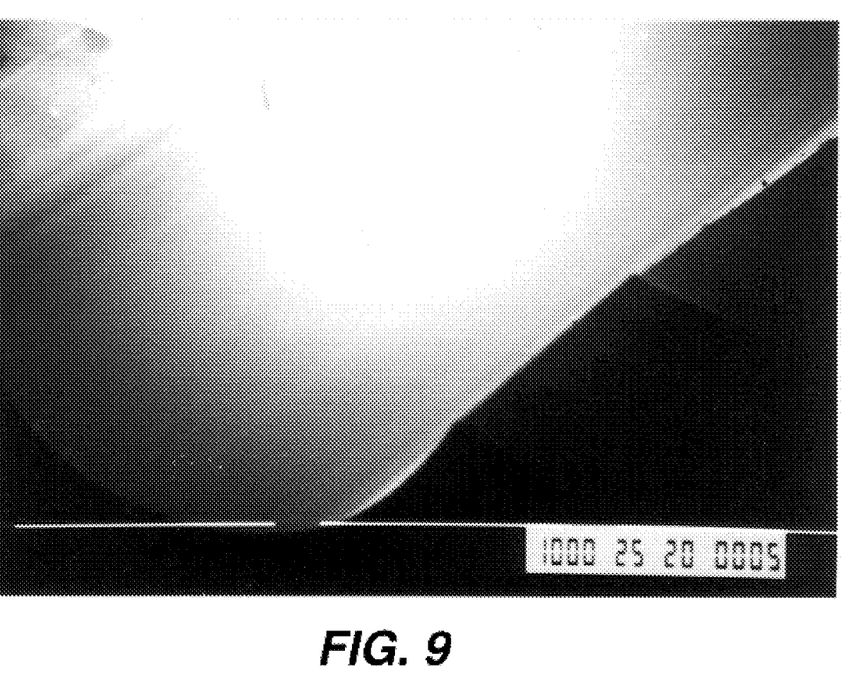
FIG. 9 is a photograph of the wall of FIG. 8 after treatment in accordance with the invention.

FIG. 9 is a photograph of the interior surface of the tubing after treatment according to this example.

EXAMPLE 5

A cleaning solution was made from 193 ml of 3% by weight of hydrogen peroxide, 3% by weight of sodium dodecyl sulfate surfactant and 50–100 grams of water soluble sodium bicarbonate particles. The solution was brought to 600 grams with distilled water.

The cleaning solution was introduced into used dental tubing along with air from a compressor set at 30–60 psi for three minutes. The tubing was then flushed with distilled water.

Figure 10:
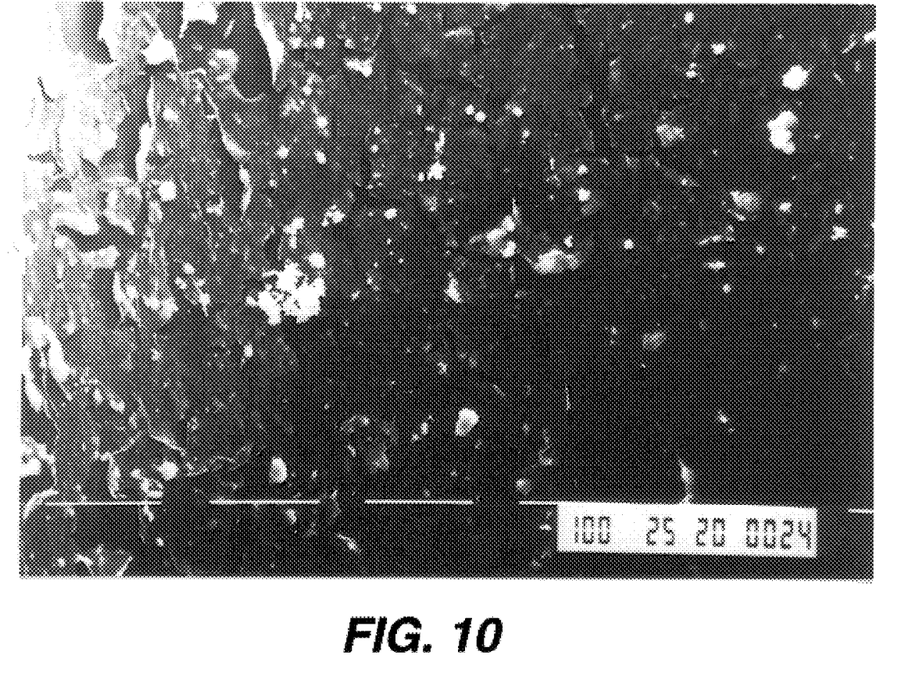
FIG. 10 is a photograph of a closeup view of another portion of dental tubing prior to treatment.
Figure 11:
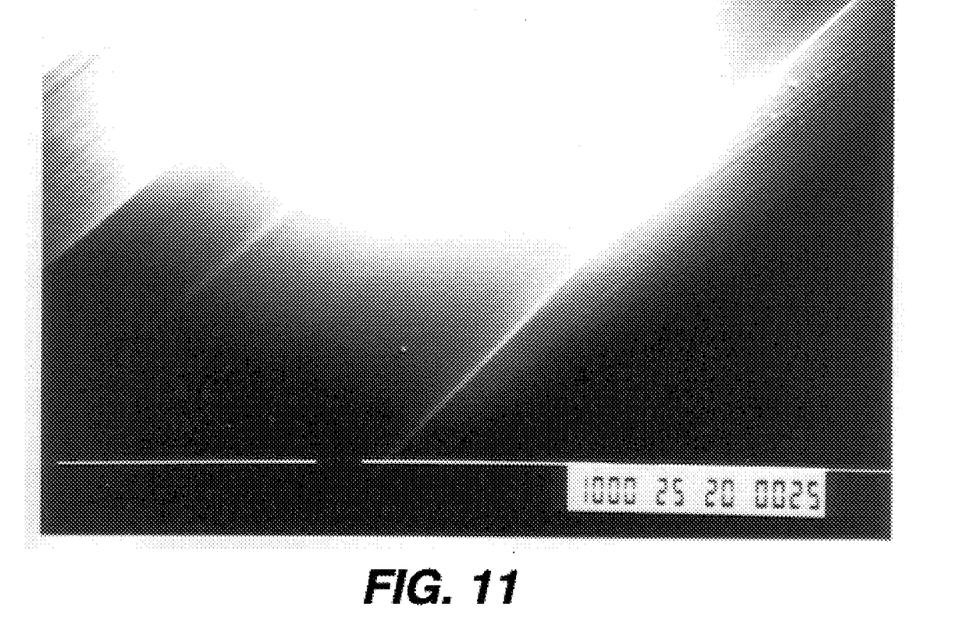
FIG. 11 is a photograph of a closeup view of the tubing of FIG. 10 after treatment in accordance with the invention.

The CFU/cm decreased from an initial value of $5.5 \times 10^4$ to zero and the CFU/ml was reduced from an initial value of $3 \times 10^6$ to zero. SEM photograph of FIG. 10 shows the presence of biofilm prior to treatment, and a complete removal of the biofilm from the lumen of the tubing after treatment, as can be seen in FIG. 11.

EXAMPLE 6

A mixture of 5% of sodium dodecyl sulfate surfactant and peroxycarbonate and 1% of polyphosphate was mixed with water to a total of 600 ml. The mixture was introduced into used dental tubing with air under pressure supplied by a compressor set at 30 to 60 psi for three minutes. The tubing was then flushed with 200 ml of water.

The CFU/cm was reduced from an initial value of $1.25 \times 10^5$ to zero and the CFU/ml was reduced from an initial value of $3 \times 10^6$ to zero.

Control

As a control, water alone was mixed with air from a compressor set at 30–60 psi and passed through used dental tubing for three minutes.

The CFU/cm was reduced from an initial value of $7.5 \times 10^4$ to $3.5 \times 10^4$. However, the CFU/ml of water was reduced only from $2.5 \times 10^6$ and was $2.38 \times 10^6$ after treatment.

Figure 12:
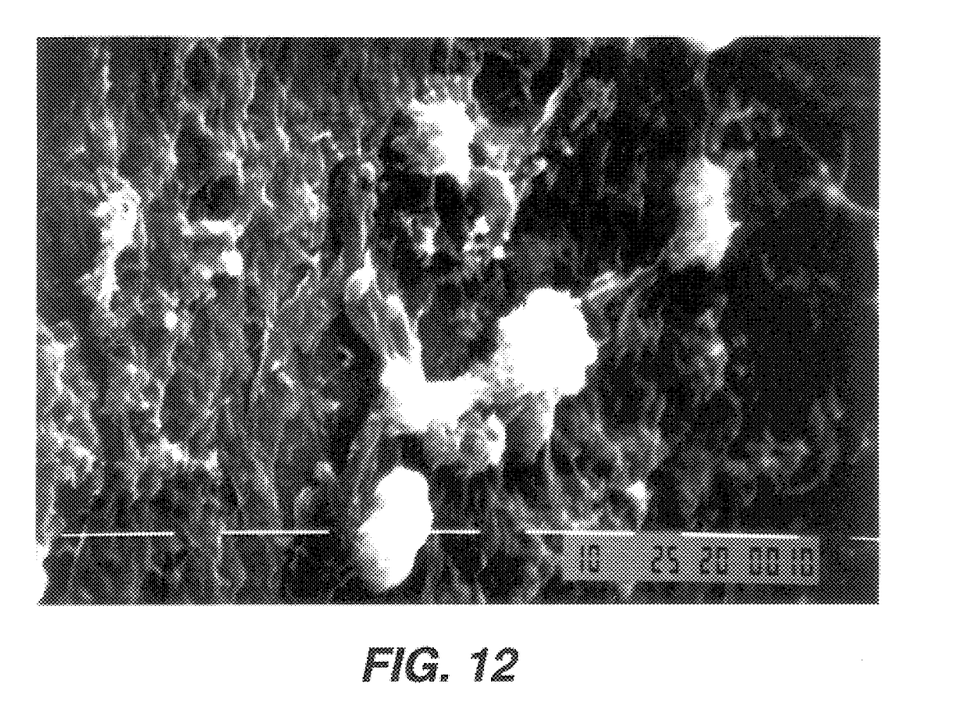
FIG. 12 is a photograph of the interior wall of still another dental tubing prior to treatment.
Figure 13:
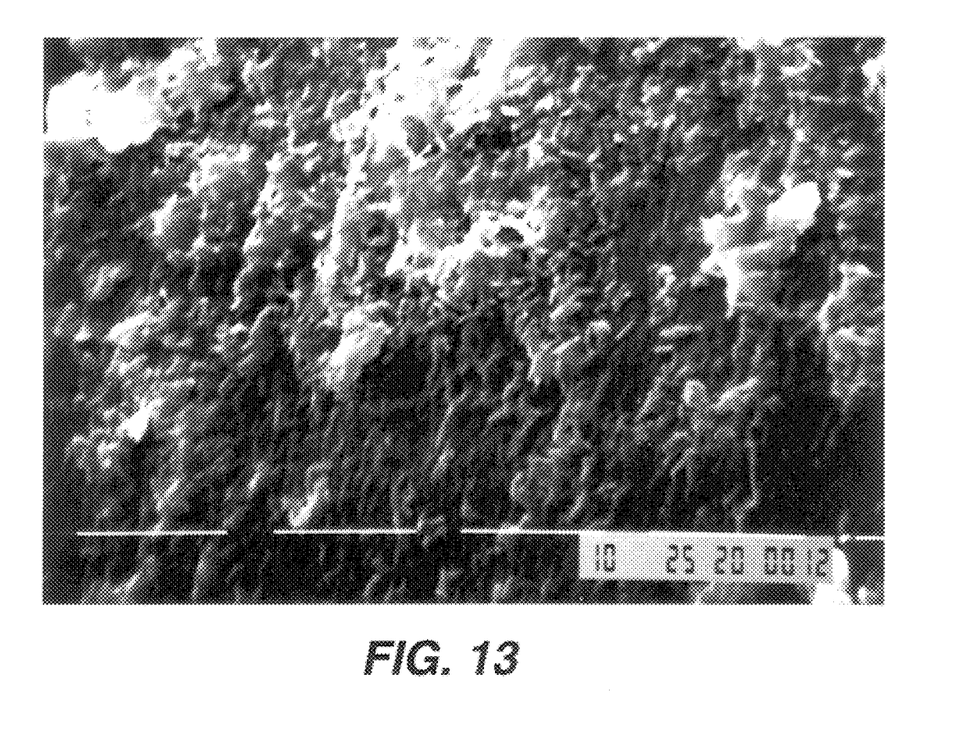
FIG. 13 is a photograph of the interior wall of FIG. 12 after treatment with a control cleaning solution.

The SEM photograph of FIG. 12 shows the presence of biofilm prior to the Control treatment and FIG. 13 shows a reduction of only about 30% in the biofilm after treatment.

Thus physical force of air and water alone is not sufficient to adequately remove biofilm from tubing.

In order to adequately maintain dental or medical tubing without substantial biofilm accumulation, the above treatment should be repeated at least about every 100 hours.

As biofilm ages, bacteria colonies not only multiply, but they become more adherent to the surface of the tubing. Thus, if treatment is repeated often, e.g., every 4–5 days, the biofilm remains comparatively easy to remove with the composition and process of the invention.

The present cleaning solutions and method can also be used to remove other contaminants in addition to biofilm from tubing, such as organic films, mucous or solid debris, e.g., tissue, loose cells, food particles and the like, that adhere to tubing walls.

Figure 14:
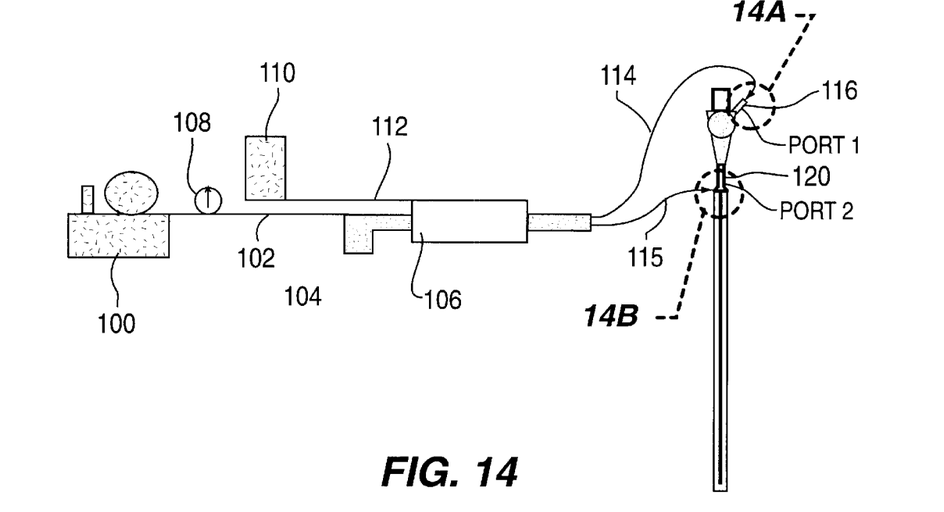
FIG. 14 is a schematic view of an apparatus used to remove biofilm and debris from the internal and external surfaces of endoscopy tubing.

A major application for such cleaning is endoscopy tubing, which in accordance with the present invention can be cleaned on both interior and exterior walls. FIG. 14 is a schematic view of a cleaning apparatus that can be used to clean both the interior walls of an endoscopy tube and the exterior walls.

Figure 14A:
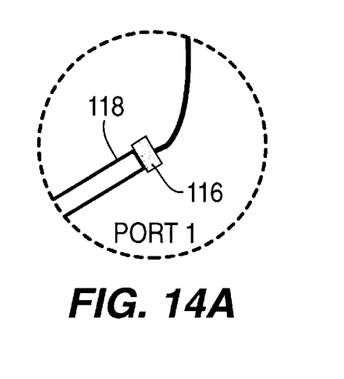
FIG. 14A is a magnified view of a port leading to the interior of the endoscopy tube.

An air compressor 100 carries air in line 102 through a compressed air pulsation control nozzle 104 to a mixing chamber 106. A pressure regulator 108 controls the air flow. A chamber 110 for the storage of cleaning solution passes the cleaning solution to the mixing chamber 106 through a line 112. The resultant turbulent mixture of pressurized air and cleaning solution is passed via line 114 to an adaptor 116 (see FIG. 14A) that provides a pressure-tight fitting to the port 118 of the endoscopy tube 120. FIG. 14A is a magnified view of the adaptor 116 and the endoscopy port 118.

Figure 14B:
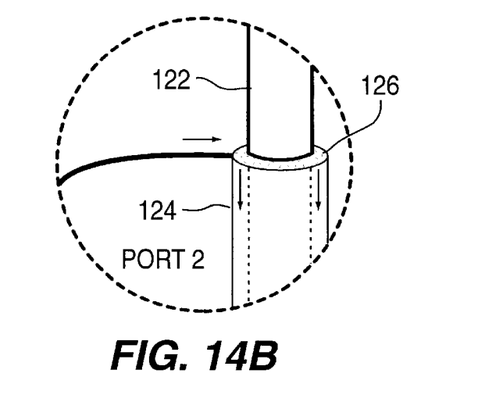
FIG. 14B is a magnified view of a port connecting the exterior wall of the endoscopy tube with a sleeve.

FIG. 14B is a magnified view of an external port 122 that fastens a pressure-tight sleeve 124 by means of an adaptor 126 to accommodate the line 115 carrying cleaning solution to the external surfaces of the endoscopy tube. The sleeve 124 can be made of any flexible plastic such as cellulose materials, polyolefins and polyesters.

Using the apparatus of FIG. 14, FIG. 14A and FIG. 14B, the following examples were carried out to clean endoscopy tubing.

EXAMPLE 7

Figure 15:
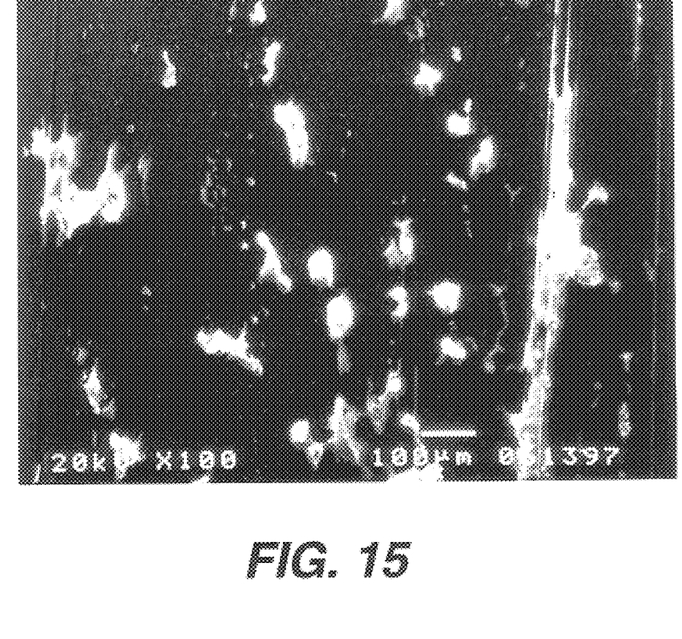
FIG. 15 is a photograph of the interior of an endoscopy tube prior to cleaning.

A flexible tubing having a length of about 6 feet and an internal channel diameter of about 0.110 cm was partially filled with a debris mixture of food residue including carbohydrates (starch), proteins and sugars and allowed to dry overnight. This residue was designed to simulate debris remaining after an endoscopy procedure. The debris can be clearly seen in FIG. 15, which is a low magnification view.

In a first step, the internal channels were filled with water for 5–10 minutes to soften the debris residue.

A mixture of cationic surfactants of 0.05% octyldecyldimethyl ammonium chloride, 0.025% dioctyldimethyl ammonium chloride and 0.025% didecyldimethyl ammonium chloride and about 1% of nonionic and anionic surfactants mixed with 4% of hydrogen peroxide were used as the cleaning solution. 500 Ml of this solution was mixed with air up to 80 psi pressure and passed through the channel over a 5 minute period.

The channels were then flushed with one liter of water.

Figure 16:
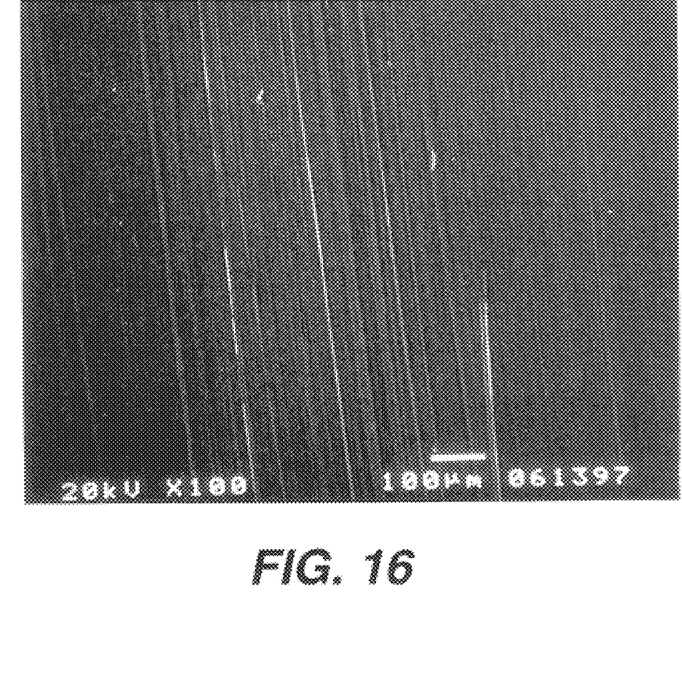
FIG. 16 is a photograph of the interior of an endoscopy tube after cleaning in accordance with the invention.

The channels were then disinfected using 200 ml of a solution of 3–7% hydrogen peroxide together with pressurized air. The channels were then dried in air for five minutes. The interior walls of the tubing were cleaned of all debris, as shown in FIG. 16.

EXAMPLE 8

The procedure of Example 7 was repeated except the cleaning solution contained a mixture of both anionic and nonionic surfactants at up to 2% concentration in a solution of 3% hydrogen peroxide. All debris was removed.

EXAMPLE 9

The procedure of Example 7 was repeated except the cleaning solution was made by first dissolving the surfactants in distilled water. All debris was removed.

EXAMPLE 10

The procedure of Example 7 was repeated except that 5% of calcium carbonate particles having a particle size of 50–200 microns was dispersed in the cleaning solution. All debris was removed.

EXAMPLE 11

The procedure of Example 8 was repeated except that 5% of calcium carbonate particles having a particle size of 50–200 microns was dispersed in the cleaning solution. All debris was removed.

Water soluble particles, such as sodium bicarbonate, can be substituted for the water insoluble calcium carbonate particles.

EXAMPLE 12

Figure 17:
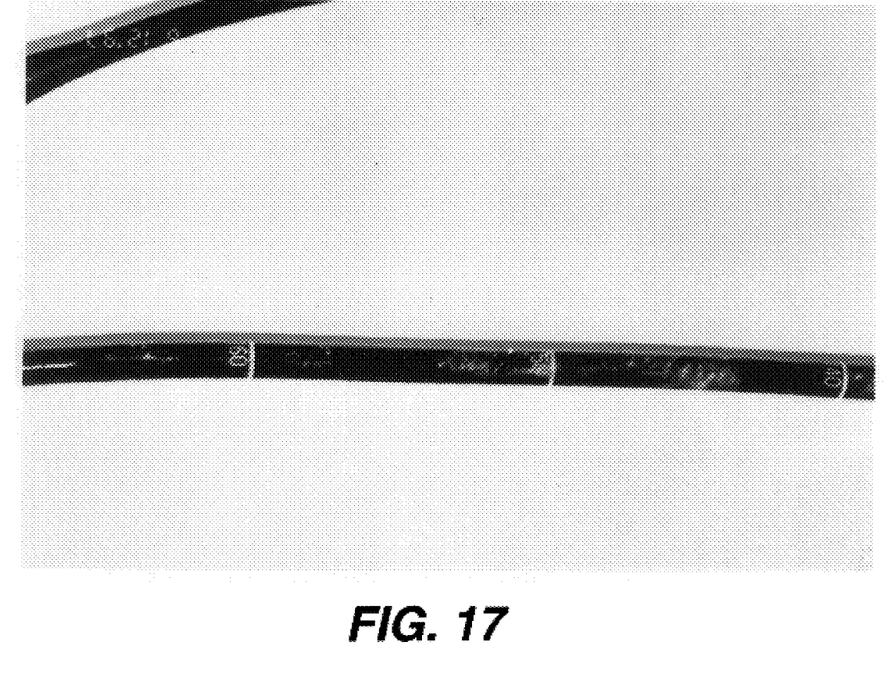
FIG. 17 is a photograph of the exterior of an endoscopy tube prior to cleaning.

The external surface of an endoscopy tube about 7 feet long and having an external diameter of 1.1 cm was immersed in a mixture of debris as in Example 7 and allowed to dry overnight. The photograph of FIG. 17 clearly shows the adhered debris on the external surface of the tubing.

Figure 18:
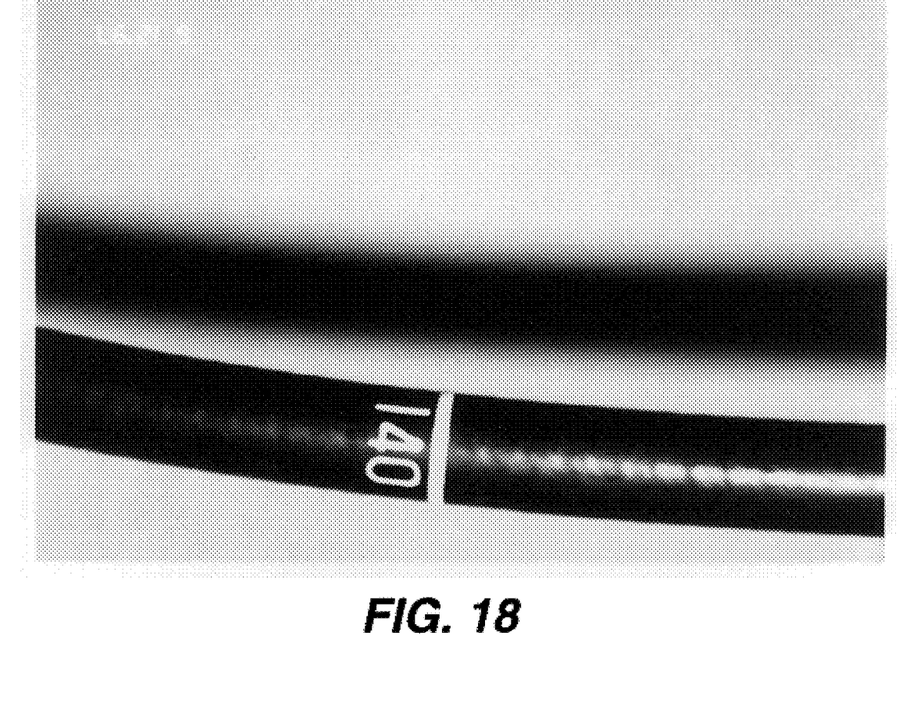
FIG. 18 is a photograph of the exterior of an endoscopy tube after cleaning in accordance with the invention.

The stem of the tube was inserted into a flexible cellulose polymer sleeve having a diameter of 1.4 cm. The sleeve and the tube were connected together by means of a pressure-tight adaptor. The cleaning solution (500 ml) of Example 7 was mixed with air at up to 100 psi pressure and passed into the sleeve for five minutes. A water flushing cycle, disinfecting cycle and drying cycle were carried out as in Example 7. All debris was removed from the external surface of the tubing as can be seen in FIG. 18.

The present cleaning solution can also be sprayed under pressure onto a surface to be cleaned, such as prosthesis implants and respirators for both adults and for neonatal care.

Although the invention has been described in terms of specific embodiments, the invention is not meant to be so limited. The invention is only to be limited by the scope of the appended claims.

What is claimed is:

1. An apparatus for removing biofilm and debris from dental unit waterlines connected to a dental chair comprising
   a source of gas under pressure;
   a source of an aqueous cleaning solution including one or more surfactants;
   means for delivering said gas to the dental unit waterlines;
   means for introducing a quantity of said cleaning solution into said gas so as to form a turbulent two-phase flow of gas and liquid having a velocity sufficient to loosen the biofilm and debris from the tubing walls and flush them away.

2. An apparatus according to claim 1 wherein the Reynolds number of the two phase mixture is above 9700.

3. An apparatus according to claim 2 wherein the Reynolds number of the two phase mixture is from about 9700 to about 15,000.

4. An apparatus according to claim 1 wherein the volumetric gas to liquid ratio is at least 50:1.

5. An apparatus according to claim 1 wherein said gas under pressure is pulsed.

6. An apparatus according to claim 1 wherein said surfactants include cationic surfactants.

7. An apparatus according to claim 1 wherein said surfactants include anionic surfactants.

8. An apparatus according to claim 1 wherein said surfactants include nonionic surfactants.

9. An apparatus according to claim 1 wherein said cleaning solution includes an oxidizing agent.

10. An apparatus according to claim 9 wherein said oxidizing agent is hydrogen peroxide.

11. An apparatus according to claim 9 wherein said cleaning solution further includes a biocide.

12. An apparatus according to claim 1 wherein said cleaning solution includes solid particles.

13. An apparatus according to claim 12 wherein said solid particles are water insoluble.

14. An apparatus according to claim 12 wherein said solid particles are water soluble.

15. An apparatus according to claim 1 wherein said gas is supplied from a compressor set at a pressure of 30 to 60 psi.

16. An apparatus according to claim 1 further including a source of water that can be added to said gas to flush the tubing walls.

17. An apparatus for removing biofilm and debris from waterlines comprising
   a source of gas under pressure;
   a source of an aqueous cleaning solution including one or more surfactants and solid particles;
   means for delivering said gas to said waterlines;
   means for introducing that quantity of said cleaning solution to said waterlines in a ratio so as to form a turbulent two-phase flow of gas and liquid having a velocity sufficient to loosen the bilfilm and debris from said waterlines and flush them away.

18. An apparatus for removing biofilm and debris from waterlines comprising
   a source of gas under pressure;
   a source of an aqueous cleaning solution including one or more surfactants;
   means for pulsing and delivering said gas to said waterlines;
   means for introducing that quantity of cleaning solution into said gas so as to form a turbulent two-phase flow of gas and liquid having a velocity sufficient to loosen the bilfilm and debris from the tubing walls and flush them away.

* * * * *